United States Patent
Gershon et al.

(10) Patent No.: US 7,205,423 B1
(45) Date of Patent: Apr. 17, 2007

(54) PROCESS FOR THE PREPARATION OF ORGANO-MOLYBDENUM COMPOUNDS

(75) Inventors: Daniel Gershon, Terryville, CT (US); Shaun Jeremy Ensor, East Haven, CT (US); Michael James St. Pierre, Waterford, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 0 days.

(21) Appl. No.: 11/385,291

(22) Filed: Mar. 21, 2006

Related U.S. Application Data

(60) Provisional application No. 60/720,260, filed on Sep. 23, 2005.

(51) Int. Cl.
*C07F 11/00* (2006.01)
*C10M 159/08* (2006.01)

(52) U.S. Cl. .................... 556/57; 508/362; 508/367
(58) Field of Classification Search ............ 556/57; 508/562, 567
See application file for complete search history.

(56) References Cited

U.S. PATENT DOCUMENTS

| 4,164,473 | A | * | 8/1979 | Coupland et al. | ............ | 508/362 |
| 4,889,647 | A | * | 12/1989 | Rowan et al. | ............ | 508/367 |
| 5,137,647 | A | * | 8/1992 | Karol | ............ | 508/367 |
| 5,412,130 | A | * | 5/1995 | Karol | ............ | 556/57 |
| 6,403,538 | B1 | * | 6/2002 | Ozaki et al. | ............ | 508/367 |

* cited by examiner

*Primary Examiner*—Porfirio Nazario-Gonzalez
(74) *Attorney, Agent, or Firm*—Norris McLaughlin & Marcus PA

(57) ABSTRACT

This invention is a process for preparation of 2,4-heteroatom-substituted molybdena-3,3-dioxocycloalkane compounds by reacting diol-, diamino, thiol-alcohol- and amino-alcohol-compounds with the following reagents:
  ammonium molybdate (or in situ produced ammonium molybdate by the reaction of ammonia with molybdenum trioxide or molybdic acid) as a molybdenum source,
  ammonia as an additional or secondary reagent or promoter, in molar ratio $NH_3$:Mo (amount of molybdenum in the molybdenum source) of $\geq 1:1$, preferably 1–3:1, more preferably 2–3:1, and most preferred 2.2–2.65:1.

18 Claims, 3 Drawing Sheets

PROCESS FOR THE PREPARATION OF ORGANO-MOLYBDENUM COMPOUNDS

BACKGROUND OF THE INVENTION

1. Field of the Invention

The invention relates to the preparation of 2,4-heteroatom-substituted molybdena-3,3-dioxocycloalkane compounds by reacting diol-, diamino, thiol-alcohol- and amino-alcohol-compounds.

2. Description of the Prior Art

U.S. Pat. No. 5,412,130 (Karol) describes a process for the preparation of molybdates (2,4-heteroatom substituted-molybdena-3,3-dioxacycloalkane compounds) by reacting the intended substrate with molybdenum source and in the presence of any proportion of phase transfer agent of the imidazoline type. The original composition of matter patent for the molybdates is under U.S. Pat. No. 4,889,647 (Rowan, Karol, and Farmer).

U.S. Pat. No. 3,285,942 (Price et. al.) describes an improved process for the manufacture of molybdenum complexes of monoglycerides with an "organic nitrogen base" selected from alkylamines having at least 6 carbons selected from aryl-, N-dialkyl amides, azines and oxazines, and said nitrogen base being added to the reaction material in an amount of 1–50% weight percent of the amount of molybdenum compound used in the reaction. Also dimethylformamide is claimed.

SUMMARY OF THE INVENTION

It has been unexpectedly discovered that the level of imidazoline can be minimized or eliminated by using ammonium molybdate as the molybdenum source with the addition of small amounts of excess ammonia or alkyl amine. Additionally, hydrogen peroxide of 1 to 5 percent based on total weight of reagents added can enhance the invention process. The invention process offers advantages of process time reduction, elimination of filtration, and continuous process adaptability (versus batch processing).

Accordingly, this invention is a process for preparation of heterocyclic molybdates by reacting diol-, diamino, thiol-alcohol- and amino-alcohol-compounds with the following reagents, to produce a molybdate derivative:

- ammonium molybdate (or in situ produced ammonium molybdate by the reaction of ammonia with molybdenum trioxide or molybdic acid) as a molybdenum source,
- ammonia as an additional or secondary reagent or promoter, in molar ratio $NH_3$:Mo (amount of molybdenum in the molybdenum source) of $\geq 1$:1, preferably 1–3:1, more preferably 2–3:1, and most preferred 2.2–2.65:1.

This would be considerably more ammonia than ammonium molybdate of the prior art (U.S. Pat. No. 5,412,130), which has a 0.86:1 $NH_3$:Mo ratio. It has been deduced that when acting as an additional secondary reagent/promoter, ammonia functions to greatly facilitate the reaction process.

The invention process is compatible with the use of imidazoline derived reaction enhancers/phase-transfer-agent, as described in U.S. Pat. No. 5,412,130 (Karol), although these agents are not required for the invention process. The optimal amount of imidazoline type phase transfer for the invention process is up to 8 percent and more preferably 6–8%.

Alkylamines can be utilized with the ammonia (but at additional expense as amines are more expensive). Therefore mixtures of ammonia and amine are chemically adaptable as well.

As used in U.S. Pat. No. 5,412,130 and herein, the term diol-, diamino-, thiol-, alcohol- and amino-alcohol compound refer to compounds derived from triglycerides, poly-alpha-olefins, polypropene, polybutylene, polyisobutylene, fatty acids, fatty oils, and fatty amides. The term 2,4-heteroatom substituted-molybdena-3,3-dioxacylcoalkane-fatty acid-derived compounds herein generically describes the heterocyclic compounds obtained by reacting the diol-, diamino, thiol-alcohol- and amino-alcohol-triglyceride compounds in the presence of ammonium molybdate or trialkyl ammonium molybdate or mixtures thereof; with either no or minimal imidazoline derived phase transfer agent. Thus, the invention may also comprise a process which takes place in the absence of imidazoline derived phase transfer agent; though the invention may also utilize any amount of imidazoline, for example, up to about 20% or more, but preferably no more than about 8% of such agent.

Ammonium molybdate or trialkyl ammonium molybdate or mixtures thereof, may be made from molybdenum trioxide and water or molybdic acid. It is chemically known that molybdenum trioxide and water form molybdic acid with mild heating. Molybdic acid reacts with ammonia to form ammonium molybdate rapidly and exothermically. Therefore molybdenum oxide or molybdic acid can be used in situ with ammonia and/or trialkyl amines to form ammonium molybdate(s).

The term 2,4-heteroatom substituted-molybdena-3,3-dioxacylcoalkane-polymer-derived compounds herein generically describes the heterocyclic compounds obtained by reacting the diol-, diamino, thiol-alcohol- and amino-alcohol-substituted poly-alpha-olefins, polypropene, polybutylene, or polyisobutylene in the presence of ammonium molybdate, with or without an amount of phase transfer agent.

The invention process is disclosed for preparation of a 2,4-heteroatom-substituted-molybdena-3,3-dioxocycloalkane composition by reacting material having the structural formula:

(A)

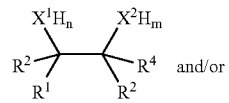
(I)

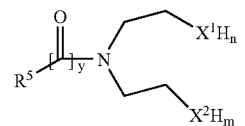
(II)

wherein $X^1$ and $X^2$ are selected from the group consisting of O, S or N and where n or m=1 when $X^1$ or $X^2$ is O or S and n or m=2 when $X^1$ or $X^2$ is N, y=0 or 1, and wherein $R^1$, $R^2$, $R^3$, $R^4$ and $R^5$ are independently selected from the group consisting of hydrogen, alkyl, alkenyl, aryl, alkylaryl hydrocarbon group or fatty residue containing from 1–50 carbon atoms or polymers having a molecular weight of 150 to 1200 and selected from poly-alpha-olefins, polypropene, polybutylene and poly isobutylene, with (B) ammonium molybdate as a molybdenum source, optionally in the presence of minimal amount of phase transfer agent of the formula:

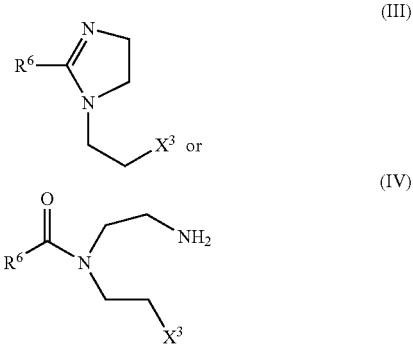

(III)

(IV)

Additionally, trace amounts (0.3–0.5%) of hydrogen peroxide were found to improve the process.

The products of these molybdate processes (prior art as well as the present invention) are believed to be a complex mixture. The prior references often simplified the complex mixture by using structures V and VI as the simplest esters envisioned (the diester of

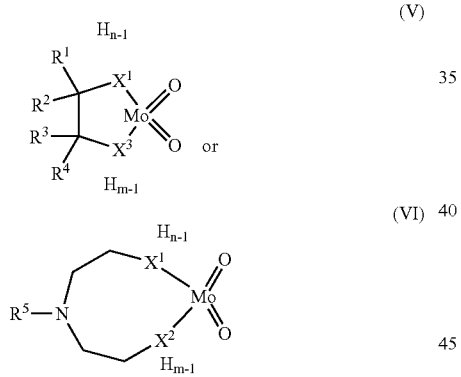

(V)

(VI)

molybdic acid in cyclic form). Since the alcohol is difunctional (diol) and molybdenum portion is multifunctional, it is possible to have highly complex product formation including oligomers, or polymer, formed in the reaction. Gel permeation analysis suggests that the molybdate product is a complex mixture with evidence of oligomerization. The degree of oligomerization as molecular weights profiles (Gel Permeation Chromatography) can be affected by processing times and temperatures. An essentially exact product of the prior art U.S. Pat. No. 5,412,130 (Karol) and U.S. Pat. No. 4,889,647 (Rowan, Karol, Farmer) can be duplicated with the present invention.

DETAILED DESCRIPTION OF THE INVENTION

Figure 1:
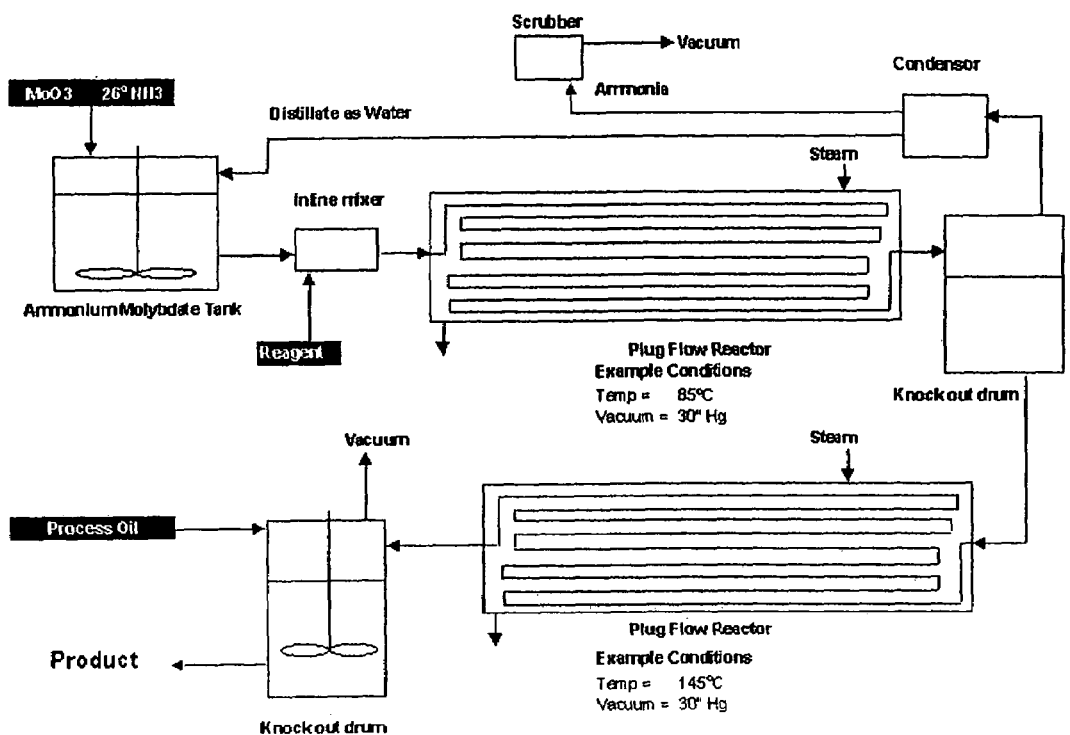
FIG. 1 shows a Plug Flow Reactor (PFR), which can be used with the present invention.

Ammonium molybdate is available commercially as $(NH_4)_6Mo_7O_{24}\cdot 4H_2O$, and the terminology "ammonium molybdate" refers to this structure in the industry. This is because the higher ammonia content in ammonium molybdate salts is typically not stable and dissociates readily, releasing ammonia gas and producing $(NH_4)_6 Mo_7O_{24}\cdot 4H_2O$. Ammonia is used in the invention as a secondary reagent or promoter. This reagent/promoter chemically shifts the equilibrium to form higher ammoniated molybdate, which are only stable in excess ammonia solution and which has been found to greatly improve the organic molybdate conversion process.

The invention uses ammonium molybdate, which can be made in situ from molybdenum trioxide reaction and ammonia (conversion to ammonium molybdate prior to addition of the alcohol substrate(s)). Since ammonia facilitates this process, an excess of ammonia is required as part of the invention. Accordingly, the process of the invention utilizes a molar ratio $NH_3:Mo$ (amount of molybdenum in the molybdenum source) of $\geq 1:1$, preferably 1–3:1, more preferably 2–3:1, and most preferred 2.2–2.65:1.

Less than about 2.07 moles ammonia to Mo will achieve improved reaction, but conversion levels may not be high enough to afford a product that does not require filtration. Levels of 1–2.07:1 are nonetheless higher ammonia content than the commercial ammonium molybdate $(NH_4)_6 Mo_7O_{24}\cdot 4H_2O$, which has a 0.86:1, $NH_3:Mo$ molar ratio. The more preferred molar ratio is therefore 2.07–2.95:1 $NH_3:Mo$, which achieves both good conversion and no filtration. The most preferred molar amount is 2.2–2.65:1, $NH_3:Mo$, because this ratio insures reproducibility of the reaction. The 2.07:1 ratio is equivalent to about 40% excess ammonia as compared to the basic stoichiometric ammonia molybdate $(NH_4)_6Mo_7O_{24}\cdot 4H_2O$. The excess ammonia is utilized herein as a secondary reagent or promoter, and amount higher than preferred levels will achieve the same process invention, though without further benefit from the additional ammonia promoter/reagent. Therefore, it is considered that higher ammonia levels, e.g. anything as a ratio to molybdenum of $\geq 1:1$ would function with the current process and therefore is considered part of the disclosed invention, though an overly excessive amount would provide no additional conversion advantage. It is envisioned that ammonia can be recycled, and in this light, further excess of ammonia may not be an economical debit. The process invention achieves remarkable batch conversion (or low hexane insoluble content because of low inorganic residue) minimizing process time and avoiding filtration.

TABLE 1

Elucidating Preferred Molar ratios, $NH_3:Mo$

| Lot | Moles Ratio NH3/MoO3 | Moles Ratio Water/MoO3 | Hex Ins |
|---|---|---|---|
| DG-1-30 | 1.83 | 23.58 | high |
| DG-1-33 | 1.85 | 23.61 | high |

TABLE 1-continued

Elucidating Preferred Molar ratios, NH₃:Mo

| Lot | Moles Ratio NH3/MoO3 | Moles Ratio Water/MoO3 | Hex Ins |
|---|---|---|---|
| DG-1-38 | 1.85 | 23.69 | high |
| DG-1-51 | 1.85 | 45.35 | did not work |
| DG-1-64 | 2.06 | 11.30 | high |
| RD-1-81 | 2.06 | 11.31 | slightly high |
| RD-1-82 | 2.06 | 11.31 | good |
| RD-1-83 | 2.07 | 11.35 | good |
| RD-1-56 | 2.09 | 28.66 | high |
| RD-1-43 | 2.10 | 24.19 | good |
| RD-1-45 | 2.10 | 24.19 | good |
| RD-1-48 | 2.10 | 20.16 | good |
| RD-1-57 | 2.10 | 24.19 | high |
| RD-1-36 | 2.10 | 28.74 | high |
| RD-1-39 | 2.10 | 28.74 | good |
| RD-1-78 | 2.21 | 12.12 | good |
| RD-1-77 | 2.51 | 12.79 | good |
| RD-1-75 | 2.65 | 15.12 | good |
| RD-1-76 | 2.65 | 14.17 | good |
| RD-1-59 | 2.95 | 26.11 | good |
| RD-1-61 | 2.95 | 26.11 | good |
| RD-1-63 | 2.95 | 26.11 | good |
| RD-1-65 | 2.95 | 26.11 | good |
| RD-1-69 | 2.95 | 23.17 | good |
| RD-1-66 | 2.95 | 25.14 | good |
| RD-1-70 | 2.95 | 22.23 | good |
| RD-1-71 | 2.95 | 21.28 | good |
| RD-1-73 | 2.95 | 18.44 | good |
| RD-1-74 | 2.95 | 16.54 | good |
| RD-1-68 | 2.95 | 24.12 | good |
| RD-1-72 | 2.95 | 20.33 | good |
| DG-1-21 | 2.95 | 26.11 | good |

The above table demonstrates ratios of NH₃:Mo to achieve product not requiring filtration (hexane insoluble <0.1% have a "good" designation).

Process technology under U.S. Pat. No. 5,412,130 (Karol) can have failure due to the build up of solid during the later stages of the water removal strip. A solid precipitate was always noticed when utilizing ammonium molybdate as the molybdenum source. However, unlike the Karol process, this solid re-dissolves during the reaction stage of the new process. Filtration is a significant delay in the time to process. The new invention offers the ability to avoid filtration completely.

Below is a list of batches produced using the new process. Consistently, though unexpectedly in view of the prior art, no filtration is needed by this new process invention. Accordingly, the invention process may also be characterized as one that produces organo-molybdenum product in the absence of a filtration step.

TABLE 2

| Lot | g H2O | g MoO3 | g NH₃ | g Reagent | Moles NH₃:Mo | G Oil | g Product | IR | Hex Ins % | % Mo | % N | % Sediment |
|---|---|---|---|---|---|---|---|---|---|---|---|---|
| RD-1-59 | 167.1 | 68.8 | 81.5 | 550 | 2.94 | 40 | | 0.13 | 0.04 | 7.4 | 3.4 | 0.1 |
| RD-1-61 | 167.1 | 68.8 | 81.5 | 550 | 2.94 | 40 | | 0.13 | 0.04 | 7.3 | 3.4 | 0.075 |
| RD-1-63 | 167.1 | 68.8 | 81.5 | 550 | 2.94 | 40 | | 0.15 | 0.04 | 7.3 | 3 | 0.1 |
| RD-1-65 | 167.1 | 68.8 | 81.5 | 550 | 2.94 | 40 | | 0.25 | 0.05 | 7.3 | 3 | 0.1 |
| RD-1-66 | 163.0 | 70.7 | 83.7 | 550 | 2.94 | 40 | | 0.21 | 0.09 | 7.5 | 2.7 | 0.15 |
| RD-1-68 | 154.8 | 71.0 | 84.1 | 550 | 2.94 | 40 | | 0.17 | 0.04 | 7.5 | 3 | 0.15 |
| RD-1-69 | 146.1 | 70.9 | 84.0 | 550 | 2.94 | 40 | | 0.12 | 0.03 | 7.5 | 3 | 0.15 |
| RD-1-70 | 136.5 | 70.3 | 83.2 | 550 | 2.94 | 40 | 629 | 0.08 | 0.03 | 7.6 | 3.1 | 0.15 |
| RD-1-71 | 154.0 | 84.4 | 100.0 | 662 | 2.94 | | 724 | 0.07 | 0.04 | 8 | 3.3 | 0.15 |
| RD-1-72 | 118.4 | 69.4 | 82.2 | 550 | 2.94 | 40 | 623 | 0.15 | 0.04 | 7.4 | 3 | 0.25 |
| RD-1-73 | 102.8 | 70.0 | 82.9 | 550 | 2.94 | 40 | 630 | 0.1 | 0.03 | 7.7 | 2.7 | 0.25 |
| RD-1-74 | 88.7 | 72.0 | 85.3 | 550 | 2.94 | 40 | 652 | 0.06 | 0.04 | 7.5 | 2.7 | 0.4 |
| RD-1-75 | 83.1 | 73.0 | 77.9 | 550 | 2.65 | 40 | 650 | 0.1 | 0.05 | 7.5 | 3.2 | 0.5 |
| RD-1-76 | 73.0 | 71.6 | 76.4 | 550 | 2.65 | 40 | 630 | 0.21 | 0.00 | 7.5 | 3.2 | 0.025 |
| RD-1-77 | 62.9 | 70.8 | 71.3 | 550 | 2.50 | 41 | 602 | 0.13 | 0.03 | 7.5 | 3.4 | 0.15 |
| RD-1-78 | 62.4 | 70.2 | 62.4 | 550 | 2.21 | 40 | 617 | 0.4 | 0.03 | 7.5 | 3.5 | 0.1 |
| RD-1-79 | 64.0 | 72.0 | 64.0 | 550[6] | 2.21 | 40 | 641 | 0.06 | 0.02 | 7.7 | 3.2 | 0.25 |
| RD-1-80 | 64.0 | 72.0 | 64.0 | 550[4] | 2.21 | 40 | 640 | 0.15 | 0.01 | 7.7 | 3.2 | 0.05 |
| RD-1-81 | 62.4 | 75.2 | 62.4 | 550[2] | 2.06 | 40 | | 0.15 | | 7.8 | 3.1 | 0.3 |
| RD-1-82 | 62.9 | 75.8 | 62.9 | 550 | 2.06 | 45 | 610 | 0.13 | 0.03 | 7.5 | 3.3 | 0.35 |
| RD-1-83 | 62.9 | 75.8 | 62.9 | 550 | 2.06 | 45 | 579 | 0.08 | 0.07 | 8.1 | 3.5 | 0.35 |
| RD-1-84 | 68.7 | 77.3 | 64.08 | 550 | 2.06 | 40 | | 0.25 | | 7.9 | 3.3 | 0.1 |
| DG-1-62 | 105 | 118.2 | 105 | 860 | 2.21 | 60 | 987 | 0.094 | | 7.8 | 3.6 | 0.3 |
| DG-1-64 | 66.7 | 80.5 | 66.7 | 550[0] | 2.06 | 40 | 604 | | 0.15 | 8.2 | 3.4 | 0.3 |
| DG-1-66 | 66.7 | 80.5 | 66.7 | 550[0] | 2.06 | 49 | 615 | 0.46 | 0.07 | 8 | 2.7 | 0.3 |
| DG-1-70 | 133.4 | 161 | 133.4 | 1130[0] | 2.06 | 96 | 1182 | 0.27 | 0.05 | 7.9 | 3 | 0.075 |
| DG-1-71 | 133.4 | 161 | 133.4 | 1100[0] | 2.06 | 96 | 1301 | 0.12 | 0.04 | 8.1 | 3.2 | <0.05 |
| DG-1-74 | 133.4 | 161 | 133.4 | 1004[0] | 2.06 | | 1066 | 0.491 | 0.11 | 9.1 | 3.3 | 0.5 |
| DG-1-75 | 133.4 | 161 | 133.4 | 900[0] | 2.06 | | 1069 | 0.47 | 0.04 | 9.8 | 3.3 | 0.65 |
| DG-1-77 | 133.4[p] | 161 | 133.4 | 1100[0] | 2.06 | 94 | 1278 | 0.16 | 0.025 | 8.1 | 2.8 | 0.3 |
| DG-1-78 | 133.4 | 161 | 133.4 | 1100[0] | 2.06 | 94 | 1226 | 0.13 | 0.037 | 8.4 | 3.1 | 0.15 |

[6] contains 6% imidazoline
[4] contains 4% imidazoline
[2] contains 2% imidazoline
[0] contains 0% imidazoline
[p] contains 30 g of 35% hydrogen peroxide in water
[a] 29.4% mass ammonia in water Reagent=reagent mixture containing 92–94% (cocodiethanolamide and coco-monoglyceride prepared by reacting coconut oil and diethanol amine) and 6–8% 1-(2-hydroxyethyl)-2-imidazoline tall oil. "Oil" may be present as a diluent, and may be of the type described in U.S. Pat. No. 5,412,130 (Karol), which is incorporated herein by reference.

Imidazoline is described in the prior art U.S. Pat. No. 5,412,130 (Karol) as an essential promoter that improved the phase transfer of molybdenum from the aqueous to the organic phase and is claimed in all proportions. The invention in this application successfully produced conversion with low or no imidazoline, provided that a vacuum is in place, prior to temperature elevation, sufficient to remove water and avoid detrimental hydrolysis in the water removal strip.

High molybdenum content of 10% or greater can be achieved by this improved process for mixtures of cocodiethanolamide and coco-monoglyceride (coconut-oil diethanolamine derived derivatives).

The process without trace amount of hydrogen peroxide affords product not requiring filtration (low hexane insolubles material commonly referred to as low hexane "insolubles") but it is still desirable to produce the least amount of hexane insolubles as possible (striving for complete conversion of the reaction by converting inorganic hexane insoluble materials to products with hexane solubility). In the invention process, hydrogen peroxide will afford conversions with exceptionally low hexane insolubles (0.025%). Hydrogen peroxide is believed to stabilize ammonium molybdate during processing.

The process time is an important consideration in chemical manufacturing and the shorter the process time (faster to make) of a chemical the more desirable for cost considerations (a faster process typically reduces cost). It was determined that the invention's process time is significantly shorter than the prior art.

TABLE 3

Invention Process Reaction Time Advantage comparisons

| | Prior Art U.S. Pat. No. 5,412,130 | Current Invention |
|---|---|---|
| Coconut Oil diethanol amine reaction product consisting of essentially Cocodiethanolamide and coco-monoglyceride | 314.6 grams | 900 grams |
| 1-(2-hydroxyethyl)-2-imidazoline derived from 50:50 oleic:linoleic acid | 27.4 grams | 0 grams |
| Molybdenum trioxide | 49.9 grams | 161 grams |
| Water | 63.4 grams | 133.4 grams |
| 29.4% ammonia in water | 0 | 133.4 grams |
| 7 Hour @ 80 C.; Hexane insoluble results | 0.25% | No pre-reaction required |
| 9 Hour @ 80 C.; Hexane insoluble results | 0.07% | No pre-reaction required |
| | 1.5 hour vacuum strip @ 90 C. | 25–35 minutes vacuum strip @ 90 C. |
| | 2 hour vacuum strip @ 135 C. | 20–30 minutes vacuum strip @ 148 C. |
| Final Hexane Insolubles | <0.10 | 0.04 |
| % molybdenum | 8.6% Mo | 9.6% Mo |
| Total reaction time | 12.5 hours | 1 hour |

The ammonium molybdate utilized in the current invention as shown in the above table is prepared in situ by initial charge of water, ammonia, and molybdenum trioxide which converts rapidly and exothermically to ammonium molybdate with excess ammonia (one minute stir). The water of reaction is slowly produced in the prior art and molybdenum incorporation is measured by hexane insoluble material (commonly referred to as "hexane insolubles"). The inorganic molybdenum must be below 0.20% to be considered a good reaction conversion and filtration with little plugging of the filter. Hexane insoluble levels below 0.10% typically require no filtration as this low level meets the specification of "filtered" product. Therefore by the comparison in the table above, the prior art process requires lengthy reaction time as compared against the invention process. Additionally the invention offers exceptionally low hexane insoluble material indicating exceptional conversion and thus no filtration step is required.

Figure 3:
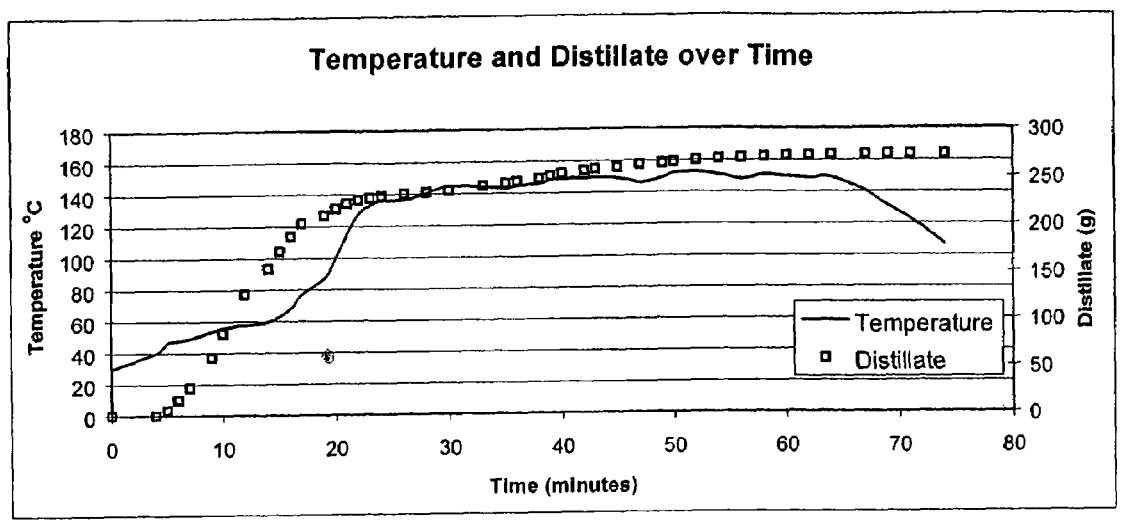
FIG. 3 is a graph showing temperature and distillate over process time.

Another advantage of the invention process is that a smooth removal of water is evident. The distillate and temperature profiles of the process were observed and are recorded in the graph shown in FIG. 3. Once the reaction reaches 54° C., water distillation removal goes rapidly until most of the water has been overhead collected.

Figure 4:
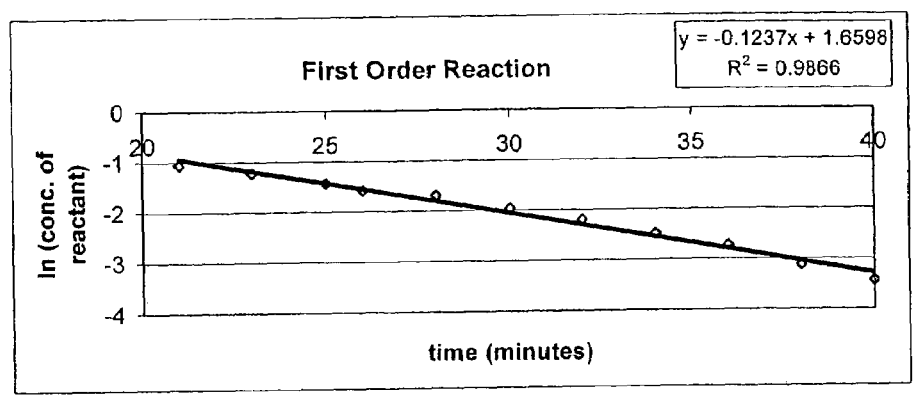
FIG. 4 is a graph showing the natural log of the reactant concentration versus time.

Water is produced during the reaction of ammonium molybdate and precursor diols. Since at lower temperatures it is hard to distinguish between excess water and product water, the water of reaction modeling was only started when the overall temperature hit 136° C. The model does not take into account temperature changes. The chart in FIG. 4 shows the natural log of the reactant concentration versus time in order to figure out the rate constant, k, for the reaction. The rate constant for a first order reaction is the slope.

Figure 5:
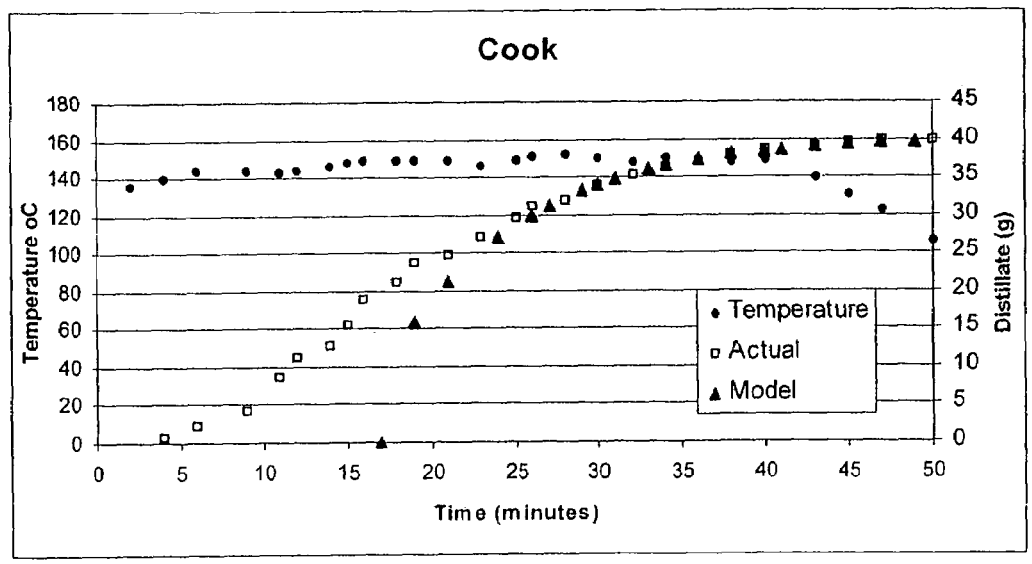
FIG. 5 is a graph showing conversion as a function of time and temperature.

Using this rate constant value, $-0.1237$ min$^{-1}$, the graph of FIG. 5 for the conversion was produced. The time scale was reset for this chart.

Another advantage of the new process invention is that the distillate from previous batches may be recycled. Three repeated experiments demonstrated that using the distillate from the previous batch as water affords conversion without disposal of distillate.

Another unexpected utility and advantage of the invention process is the adaptability to continuous processing. Typically chemical batches are made in lots where a certain amount of material is converted to the desired product batch by batch. In adaptation to continuous processing, simply put, the reagents are fed in at one end of the process and the product comes out the other end.

Figure 2:
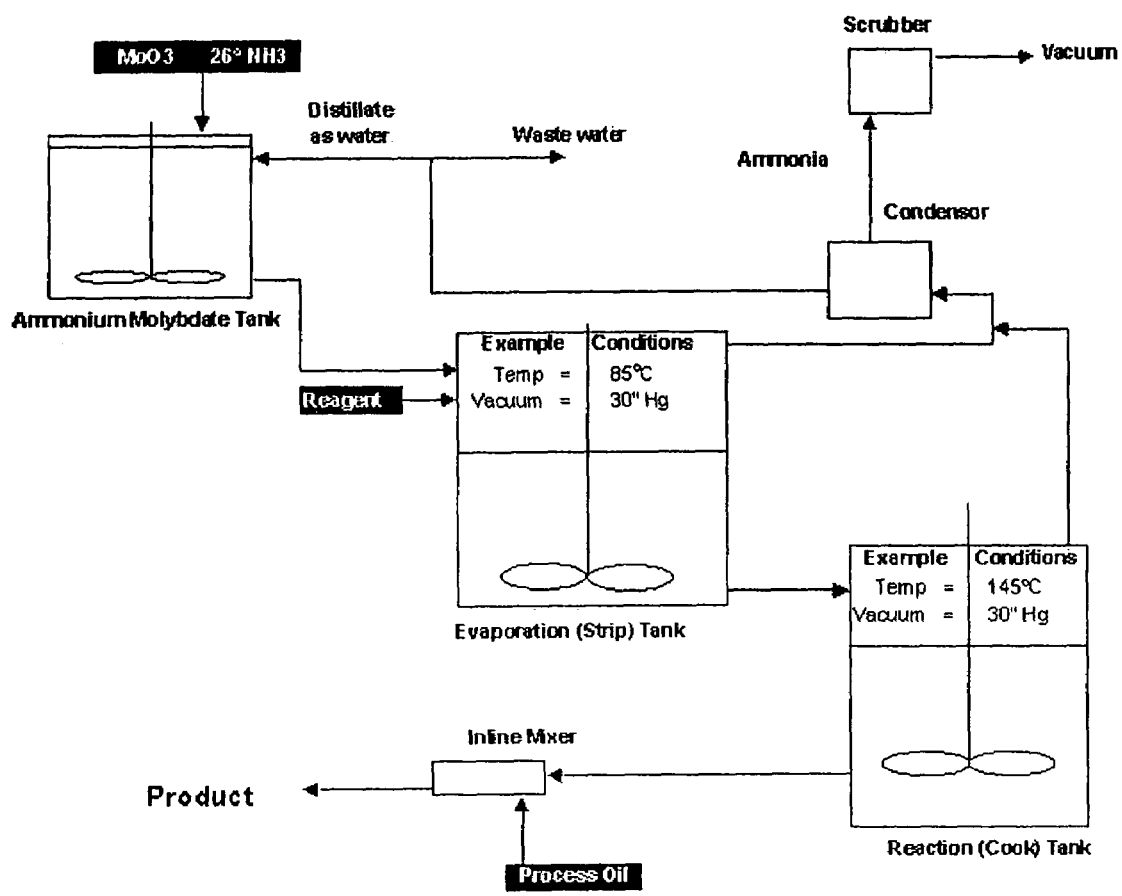
FIG. 2 shows a Continuous-flow Stirred Tank Reactor (CSTR), which can be used with the present invention.

The continuous process would consist of either plug flow reactors, PFRs (also called tubular reactors) (see FIG. 1), continuous-flow stirred tank reactors, CSTRs (see FIG. 2), or a mixture of PFRs and CSTRs.

The process would have an evaporation (or stripping) stage where the water and excess ammonia are removed from the reactants. This could be done using a PFR or a CSTR. Following the stripping stage, the reactants would then flow into another reactor where they would be reacted; again this could be done in a PFR or a CSTR. In a CSTR process reactants are charged to and the products are removed from the reactor continuously. Inlet reactants are dispersed quickly due to quick agitation, and the composition at any point is equal to the average composition of the system. The time needed for the reaction or evaporation to take place is called the residence time. So, the size of the reactor would have to be greater than the product of the residence time and the inlet flow rate. At large residence times, reactors would have to be very large. In a PFR, the reactants enter one end of a long tube and the products exit the other end. In this case, the mixing is dependent on the fluid, the tube size and the flow rate. For a PFR, the residence time is the time it takes the fluid to enter one and exit the other. So for large residence times, longer or thicker tubes would have to be used.

One of the benefits of the CSTR method over the PFR is that it is easily converted from older batch equipment. Whereas the PFR has great potential when it comes to scaling up—since tube length, size, flow rate, and number of tubes can all be changed to increase production.

If designed correctly, both stages could take place in either one or multiple reactors, although the two-reactor process would be easier to control as each reactor is used for one stage of the process.

What is claimed is:

1. A process for preparing 2,4-heteroatom-substituted molybdena-3,3-dioxocycloalkane compounds, comprising the steps of:

reacting (A) a starting material having the structural formula

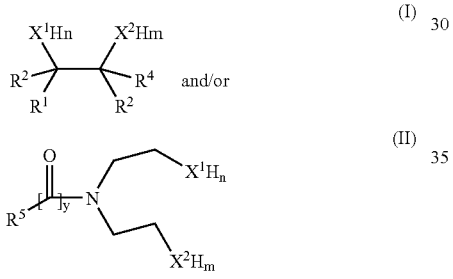

wherein $X^1$ and $X^2$ are selected from the group consisting of O, S or N and where n or m=1 when $X^1$ or $X^2$ is O or S and n or m=2 when $X^1$ or $X^2$ is N, y=0 or 1, and wherein $R^1$, $R^2$, $R^3$, $R^4$ and $R^5$ are independently selected from the group consisting of hydrogen, alkyl, alkenyl, aryl, alkylaryl hydrocarbon group or fatty residue containing from 1 to 50 carbon atoms or polymeric residues having a molecular weight of 150 to 1200; and selected from poly-alpha-olefin, polypropene, polybutylene and polyisobutylene; with:

(B) ammonium molybdate as a molybdenum source sufficient to yield about 2 to 20 percent of molybdenum based on the weight of the molybdena-compound, in the presence of water, and (C) an additional or secondary reagent or promoter in molar amount≧1:1, Z:Mo, where Z is one of or both in combination of (i) ammonia and (ii) an alkylamine where the alkyl groups are independently selected from straight or branched chain C1 to C6;

removing water; and recovering the molybdena-compounds.

2. The process of claim 1, wherein the recovered molybdena compounds comprise a complex mixture represented by a generic formula as

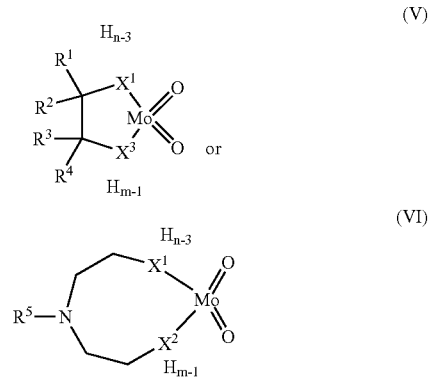

and which may optionally also contain oligomers and polymer due to the multifunctional nature of the reagents, wherein $R^1$, $R^2$, $R^3$, $R^4$, $R^5$, $X^1$, $X^2$, n and m are defined and correspond to the starting materials in formula (I) and (II).

3. The process according to claim 1, further comprising adding as an additional reagent up to 20% of a phase transfer agent of the formula

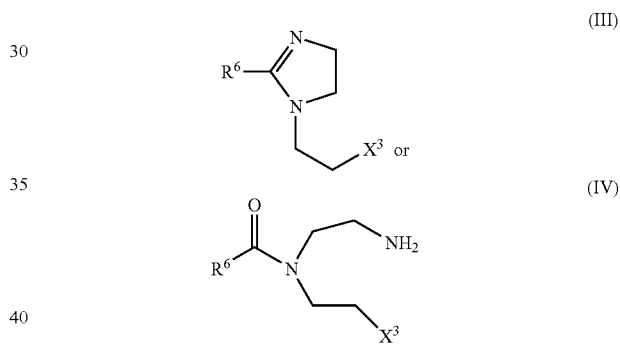

wherein $R^6$ is an alkyl group or fatty residue having 8 to 22 carbon atoms and $X^3$ is a hydroxy or amino group.

4. The process according to claim 3, wherein the phase transfer agent is added in an amount up to 8%.

5. The process according to claim 1, further comprising adding as an additional reagent hydrogen peroxide from 1 to 5 percent of 35% hydrogen peroxide or the equivalent thereof.

6. The process according to claim 4, wherein the phase transfer agent is 1-(2-hydroxyethyl)-2-octadecylimidazoline.

7. The process according to claim 1, wherein the starting material of formula I is derived from epoxidized fatty oils or fatty acids.

8. The process according to claim 1 wherein the starting material of formula I is derived from triglycerides.

9. The process according to claim 1, wherein the starting material of formula I is derived from epoxidized polymers having a molecular weight in the range of 150 to 1200 and selected from poly-alpha-olefins, polypropene, polybutylene and polyisobutylene.

10. The process according to claim 1, wherein the ammonium molybdate is produced in situ from molybdenum trioxide or molybdic acid and ammonia.

11. A process according to claim 1, wherein the reaction ratio is 1–3:1, and which further comprises a filtration step where the ratio is at a level less than 2.06:1.

12. The process according to claim 4, wherein R6 is derived from tall oil (50:50 oleic:linoleic acid).

13. The process according to claim 12, wherein the imidazoline derivative is 1-(2-hydroxyethyl)-2-imidazoline derived from 50:50 oleic:linoleic acid in an amount of 6 to 8 percent by mass.

14. The process of claim 1, wherein the reaction ratio is 1–3:1.

15. The process of claim 14, wherein the reaction ratio is 2.07–2.95.

16. The process of claim 15, wherein the reaction ratio is 2.2–2.65:1.

17. The process of claim 14, wherein Z is ammonia.

18. The process of claim 1, wherein the reaction takes place at 60 to 150° C.

* * * * *